United States Patent [19]

Crenshaw et al.

[11] 4,158,013
[45] Jun. 12, 1979

[54] N-CYANO-N'-ALKYNYL-N''-2-MERCAPTO-ETHYLGUANIDINES

[75] Inventors: Ronnie R. Crenshaw, Dewitt; George M. Luke, LaFayette, both of N.Y.

[73] Assignee: Bristol-Myers Company, New York, N.Y.

[21] Appl. No.: 906,901

[22] Filed: May 18, 1978

Related U.S. Application Data

[63] Continuation-in-part of Ser. No. 848,959, Nov. 7, 1977, Pat. No. 4,112,234, which is a continuation-in-part of Ser. No. 826,796, Aug. 22, 1977, abandoned, which is a continuation-in-part of Ser. No. 803,009, Jun. 3, 1977, abandoned.

[51] Int. Cl.² .................. C07C 125/08; C07C 129/08
[52] U.S. Cl. .......................... 260/551 C; 260/564 H
[58] Field of Search ................... 260/564 H, 551 C

[56] References Cited

U.S. PATENT DOCUMENTS

| 2,697,727 | 12/1954 | Kaiser | 260/551 C |
|---|---|---|---|
| 4,013,678 | 3/1977 | Brown et al. | 260/309 |
| 4,093,621 | 6/1978 | Brown et al. | 260/294.8 H |

FOREIGN PATENT DOCUMENTS 853954 10/1977 Belgium.

Primary Examiner—Gerald A. Schwartz
Attorney, Agent, or Firm—Richard R. Lloyd

[57] ABSTRACT

Anti-ulcer agents of the formula

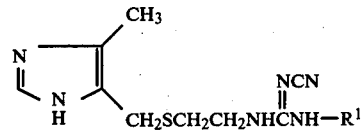

wherein $R^1$ is a straight or branched chain alkynyl group containing from 3 to 9 carbon atoms, inclusive, are prepared by reacting a compound of the formula

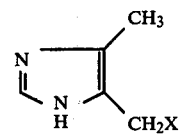

wherein X is a conventional leaving group, preferably in the form of its acid addition salt, with a compound of the formula

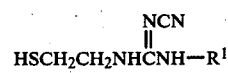

wherein $R^1$ is as defined above. The intermediates of Formula III may be prepared by reacting a cysteamine salt with an isothiourea of the formula

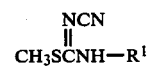

wherein $R^1$ is as described above, in the presence of a base.

10 Claims, No Drawings

N-CYANO-N'-ALKYNYL-N''-2-MERCAPTOETHYL-GUANIDINES

CROSS-REFERENCE TO RELATED APPLICATIONS

This application is a continuation-in-part of our co-pending application Ser. No. 848,959, filed Nov. 7, 1977, now U.S. Pat. No. 4,112,234, which is a continuation-in-part of our application Ser. No. 826,796, filed Aug. 22, 1977, and now abandoned, which in turn was a continuation-in-part of our application Ser. No. 803,009, filed June 3, 1977, and now abandoned.

SUMMARY OF THE INVENTION

This invention relates to a novel process for the preparation of certain N-cyano-N'-{2-[(4-methyl-5-imidazolyl)methylthio]ethyl}-N''-alkynylguanidines which are H$_2$ receptor blocking agents, which inhibit gastric acid secretion and which are useful in the treatment of ulcers. This invention also relates to novel intermediates in the preparation of the anti-ulcer agents.

BACKGROUND AND PRIOR ART

The clinical objective in treatment of peptic ulcer disease is to decrease gastric acid secretion, based on the principle "no acid, no ulcer." Traditional peptic ulcer disease therapy involves control of diet and the use of antacids and anticholinergics.

There is evidence indicating that histamine may be the final common pathway for stimulation of gastric secretion. This effect of histamine is mediated via H$_2$ receptors and is not inhibited by the classical antihistamines, which are H$_1$ receptor blockers. A number of specific H$_2$ receptor blocking agents (H$_2$ receptor antagonists) are now known. These compounds inhibit basal acid secretion, as well as secretion by other known gastric acid stimulants, and are useful in the treatment of peptic ulcers.

Burimamide (VIa) was the first clinically effective

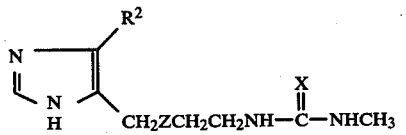

VI

VIa; R$^2$=H, Z=CH$_2$, X=S Burimamide
b; R$^2$=CH$_3$, Z=S, X=S Metiamide
c; R$^2$=CH$_3$, Z=S, X=NCN Cimetidine H$_2$ receptor antagonist. It inhibits gastric secretion in animals and man, but oral absorption is poor. Metiamide (VIb), a subsequently evaluated H$_2$ antagonist, is more potent than burimamide and is orally active in man. Clinical utility was limited, however, owing to toxicity (agranulocytosis). Cimetidine (VIc) is as effective an H$_2$ antagonist as metiamide, without producing agranulocytosis, and has recently been marketed as an anti-ulcer drug. The half-life of cimetidine is relatively short, thereby necessitating a therapeutic regimen of multi daily doses of 200 mg. tablets. There is thus a need for anti-ulcer agents which are longer acting and/or more potent than cimetidine.

Reviews on the development of H$_2$ antagonists, including those discussed in the preceding paragraph, may be found in C. R. Ganellin, et al., Federation Proceedings, 35, 1924 (1976), in Drugs of the Future, 1, 13 (1976), and in references cited therein.

Our co-pending application Ser. No. 848,959, filed Nov. 7, 1977, now U.S. Pat. No. 4,112,234 (the disclosure of which is incorporated herein by reference) describes and claims novel histamine H$_2$ receptor antagonists of the formula

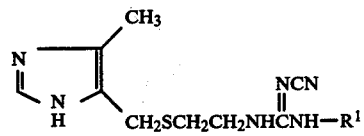

I wherein R$^1$ is a straight or branched chain alkynyl group containing from 3 to 9 carbon atoms, inclusive, and nontoxic, pharmaceutically acceptable salts thereof, which are effective inhibitors of gastric secretion in animals, including man, and which are useful in the treatment of peptic ulcer disease.

Belgian Pat. No. 853,954 (Farmdoc 77515Y) discloses and claims the following process for the preparation of histamine H$_2$ antagonists, or intermediates therefor:

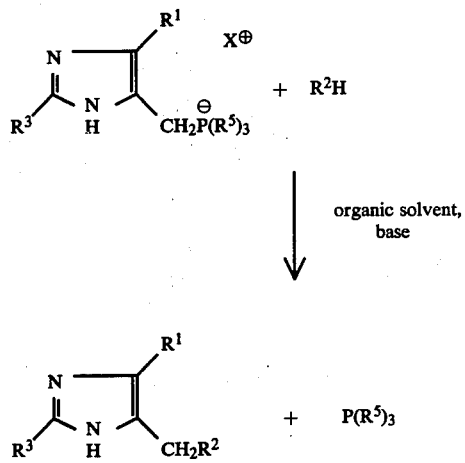

wherein R$^1$ is hydrogen or (lower)alkyl; R$^2$ is a group of the formula

or is —NR$^6$R$^7$; R$^6$ and R$^7$ are hydrogen or (lower)alkyl, or taken together with the nitrogen atom, represent piperidine, pyrrolidine or morpholine; R$^3$ is hydrogen, (lower)alkyl, trifluoromethyl, benzyl, amino or the group —SR$^4$; R$^4$ is (lower)alkyl, phenyl, benzyl or chlorobenzyl; R$^5$ is (lower)alkyl or phenyl; and X is hydrogen.

H. Erlenmeyer et al., Helvetica Chimica Acta, 31, 32–40 (1948) describe the compound

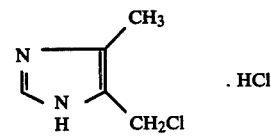

and its preparation, which is a member of one of the two classes of starting materials utilized in the process aspect of the present invention.

COMPLETE DISCLOSURE

In one aspect, this invention relates to novel intermediates of the formula

   III wherein $R^1$ is a straight or branched chain alkynyl group containing from 3 to 9 carbon atoms, inclusive, and acid addition salts thereof, which are useful in the preparation of histamine $H_2$ receptor antagonists of Formula I.

In a preferred embodiment, $R^1$ of the compound of Formula III is

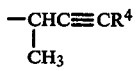

in which $R^4$ is hydrogen or methyl; in another preferred embodiment $R^1$ is $-(CH_2)_nC\equiv CR^4$ in which n is an integer of from 1 to 6 and $R^4$ is hydrogen or methyl; in another preferred embodiment $R^1$ is

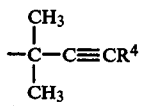

in which $R^4$ is hydrogen or methyl.

In a more preferred embodiment, $R^1$ of the compound of Formula III is the 2-butyn-1-yl group; in another more preferred embodiment $R^1$ is the 3-butyn-1-yl group; in another more preferred embodiment $R^1$ is the 4-pentyn-1-yl group; in another more preferred embodiment $R^1$ is the 2-methyl-3-butyn-2-yl group; in another more preferred embodiment $R^1$ is the 3-butyn-2-yl group. In the most preferred embodiment, $R^1$ of the compound of Formula III is the propargyl group.

In another aspect, this invention relates to a process for the preparation of a compound of the formula

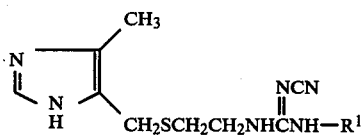   I wherein $R^1$ is a straight or branched chain alkynyl group containing from 3 to 6 carbon atoms inclusive, or a nontoxic, pharmaceutically acceptable salt thereof, which process comprises reacting a compound of the formula

   III wherein $R^1$ is as described above, with about an equimolar amount of a compound of the formula

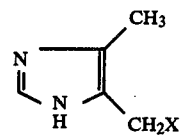   II in which X is a conventional leaving group, and preferably an acid addition salt thereof, in an inert organic solvent, and preferably in the presence of a base.

Suitable leaving groups "X" for use in this reaction are well-known to those skilled in the art. They include, for example, fluoro, chloro, bromo, iodo, $-O_3SR^2$ wherein $R^2$ is (lower)alkyl [e.g. methanesulfonate], $-O_3SR^3$ wherein $R^3$ is aryl or substituted aryl [e.g. benzenesulfonate, p-bromobenzenesulfonate or p-toluenesulfonate], $-O_3SF$, acetoxy and 2,4-dinitrophenoxy. For convenience and economy we normally prefer to utilize compound II in which X is chloro.

In the process of this invention, the compound of Formula II preferably is utilized in the form of an acid addition salt. Compound II is relatively unstable in its free base form and therefore is preferably prepared and stored as an acid addition salt. Although the free base of the compound of Formula II may be re-generated prior to the reaction, no advantage is obtained by so doing. It will be appreciated by those skilled in the art that any inorganic acid or organic acid may be utilized to form the acid addition salt of compound II, e.g. hydrochloric, sulfamic, sulfuric, oxalic, benzoic, succinic, acetic, nitric, citric or the like. For convenience and economy we normally prefer to utilize compound II in the form of its hydrochloride.

The reaction of compounds II and III to produce compound I may be conducted in any inert organic solvent such as an alkanol, acetonitrile, dimethylformamide, dimethylsulfoxide, acetone, or the like. We prefer to conduct the reaction in an alkanol such as ethanol or 2-propanol.

The reaction temperature is not critical; the reaction may be conducted at temperatures of from about 0° to about 200°. At low temperatures the reaction is slow, while high temperatures normally lead to less pure products due to decomposition and the formation of side-products. We normally prefer to conduct the reaction at room temperature.

The reaction of compounds II and III to produce compound I is preferably conducted in the presence of a base, which facilitates the reaction by acting as an acid acceptor. Suitable bases for use in this reaction include both inorganic and organic bases such as NaOH, KOH, LiOH, triethylamine, dimethylaniline, sodium ethoxide and the like.

As used herein, the term nontoxic pharmaceutically acceptable acid addition salt means the mono- or di-salt of a compound of Formula I with a nontoxic pharmaceutically acceptable organic or inorganic acid. Such acids are well known and include hydrochloric, hydrobromic, sulfuric, sulfamic, phosphoric, nitric, maleic, fumaric, succinic, oxalic, benzoic, methanesulfonic, ethanedisulfonic, benzenesulfonic, acetic, propionic, tartaric, citric, camphorsulfonic, and the like. The salts are made by methods known in the art.

As used herein, the term (lower)alkyl is intended to mean straight or branched alkyl groups containing from 1 to 6 carbon atoms.

The dimethyl cyanodithioiminocarbonate which is used as a starting material for the preparation of the N-cyano-N'-alkynyl-S-methylisothioureas may itself be prepared by procedures described in J. Org. Chem., 32, 1566 (1967). The alkynylamine starting materials are either commercially available or may be prepared by methods described in Bull. Soc. Chim. Fr., 490 (1958); Bull Soc. Chim. Fr., 592 (1967) and Annales de Chimie (Paris), 3, 656 (1958).

When reacting cysteamine hydrochloride with an N-cyano-N'-alkynyl-S-methylisothiourea to produce an N-cyano-N'-alkynyl-N''-(2-mercaptoethyl)guanidine of Formula III, it was found desirable to conduct the reaction in the presence of a small amount of hydroquinone and to bubble nitrogen through the reaction mixture (see, for example, step B of Example 1). These reaction conditions were found to produce compounds of Formula III in higher yield and of higher purity. The nitrogen sweep is believed to remove the methyl mercaptan produced in the reaction and thereby avoid secondary reactions arising from the addition of methyl mercaptan to the carbon-carbon triple bond. It is believed that the hydroquinone prevents the formation of free radicals and secondary reactions arising from their presence.

This invention is illustrated by, but in no way limited to, the following examples.

EXAMPLE 1

N-Cyano-N'-{2-[(4-methyl-5-imidazolyl)methylthio]ethyl}-N''-propargylguanidine

A. N-Cyano-N'-propargyl-S-methylisothiourea

A solution of dimethyl cyanodithioiminocarbonate (16.00 g, 0.109 mole) and propargylamine (6.03 g, 0.109 mole) in acetonitrile (320 ml) was stirred at reflux for 4 hours, and then at 25° for 12 hours. The mixture was cooled and filtered to yield the title compound (13.58 g, 81%), mp 160°–164°.

B. N-Cyano-N'-propargyl-N''-(2-mercaptoethyl)guanidine

A mixture of 1.136 g (10 m moles) of cysteamine hydrochloride, 1.53 g (10 m moles) of the product of step A, above, and 0.055 g of hydroquinone in 10 ml DMF was slightly warmed to dissolve. To this solution was added 10 ml of 1 N aqueous sodium hydroxide and nitrogen was bubbled through the solution. After standing at room temperature for 17 hours, the reaction mixture was evaporated to dryness to give a mixture of the title product and sodium chloride. The title product was extracted from this mixture with 10 ml of ethanol and the ethanolic solution was used in step C, below.

C. N-Cyano-N'-{2-[(4-methyl-5-imidazolyl)methylthio]ethyl}-N''-propargylguanidine The ethanol solution of the product of step B, above, (about 10 m moles) was added to a solution of 0.46 sodium (0.02 g-atoms) in 10 ml ethanol at 4° C. under nitrogen. After 5 minutes, a solution of 1.67 g (10 m moles) of 4-methyl-5-chloromethylimidazole.HCl in 14 ml ethanol was added and the mixture was stirred at room temperature under nitrogen for 70 minutes. The reaction mixture was filtered through a bed of celite filter aid to remove the inorganic salts and the celite was washed with ethanol. The filtrate was evaporated to dryness and the product was purified by chromatography on a silica gel column (20 g silica, 3.2×4.5 cm bed) with ethanol-chloroform mixtures as the solvent. The ethanol content was gradually increased from 2 to 15%. The eluant was evaporated to dryness to give 1.906 g of crystalline product. Recrystallization from 2-propanol gave 1.49 g (54%) of the title product, m.p. 144°–145° C.

EXAMPLE 2

N-Cyano-N'-{2-[(4-methyl-5-imidazolyl)methylthio]ethyl}-N''-(2-butyn-1-yl)guanidine

A. N-Cyano-N'-(2-butyn-1-yl)-S-methylisothiourea

A solution of dimethyl cyanodithioiminocarbonate (10.00 g, 0.0684 mole) and 2-butyn-1-amine (4.73 g, 0.0684 mole) in acetonitrile (200 ml) was stirred at 25° for 0.5 hour, and then at reflux for 2.5 hours. The mixture was cooled, then filtered to yield the title compound, mp 180°–183°.

B. N-Cyano-N'-(2-butyn-1-yl)-N''-(2-mercaptoethyl)guanidine

The general procedure of Example 1B is repeated except that the N-cyano-N'-propargyl-S-methylisothiourea utilized therein is replaced by an equimolar amount of N-cyano-N'-(2-butyn-1-yl)-S-methylisothiourea, and the title product is thereby produced.

C. N-Cyano-N'-{2-[(4-methyl-5-imidazolyl)methylthio]ethyl}-N''-(2-butyn-1-yl)guanidine The general procedure of Example 1C is repeated except that the N-cyano-N'-propargyl-N''-(2-mercaptoethyl)guanidine utilized therein is replaced by an equimolar amount of N-cyano-N'-(2-butyn-1-yl)-N''-(2-mercaptoethyl)guanidine, and the title product is thereby produced.

EXAMPLE 3

N-Cyano-N'-{2-[(4-methyl-5-imidazolyl)methylthio]ethyl}-N''-(3-butyn-1-yl)guanidine

A. N-Cyano-N'-(3-butyn-1-yl)-N''-(2-mercaptoethyl)guanidine

The general procedures of Example 1, steps A and B, are repeated except that the propargylamine utilized in step A thereof is replaced by an equimolar amount of 3-butyn-1-amine, and the title product is thereby produced.

B. N-Cyano-N'-{2-[(4-methyl-5-imidazolyl)methylthio]ethyl}-N''-(3-butyn-1-yl)guanidine The general procedure of Example 1C is repeated except that the N-cyano-N'-propargyl-N''-(2-mercaptoethyl)guanidine utilized therein is replaced by an equimolar amount of N-cyano-N'-(3-butyn-1-yl)-N''-(2-mercaptoethyl)guanidine, and the title product is thereby produced.

EXAMPLE 4

N-Cyano-N'-{2-[(4-methyl-5-imidazolyl)methylthio]ethyl}-N''-(4-pentyn-1-yl)guanidine

A.
N-Cyano-N'-(4-pentyn-1-yl)-N''-(2-mercaptoethyl)guanidine

The general procedures of Example 1, steps A and B, are repeated except that the propargylamine utilized in step A thereof is replaced by an equimolar amount of 4-pentyn-1-amine, and the title product is thereby produced.

B.
N-Cyano-N'-{2-[(4-methyl-5-imidazolyl)methylthio]ethyl}-N''-(4-pentyn-1-yl)guanidine The general procedure of Example 1C is repeated except that the N-cyano-N'-propargyl-N''-(2-mercaptoethyl)guanidine utilized therein is replaced by an equimolar amount of N-cyano-N'-(4-pentyn-1-yl)-N''-(2-mercaptoethyl)guanidine, and the title product is thereby produced.

EXAMPLE 5

N-Cyano-N'-{2-[(4-methyl-5-imidazolyl)methylthio]ethyl}-N''-(2-methyl-3-butyn-2-yl)guanidine

A.
N-Cyano-N'-(2-methyl-3-butyn-2-yl)-N''-(2-mercaptoethyl)guanidine

The general procedures of Example 1, steps A and B, are repeated except that the propargylamine utilized in step A thereof is replaced by an equimolar amount of 1,1-dimethylpropargylamine, and the title product is thereby produced.

B.
N-Cyano-N'-{2-[(4-methyl-5-imidazolyl)methylthio]ethyl}-N''-(2-methyl-3-butyn-2-yl)guanidine The general procedure of Example 1C is repeated except that the N-cyano-N'-propargyl-N''-(2-mercaptoethyl)guanidine utilized therein is replaced by an equimolar amount of N-cyano-N'-(2-methyl-3-butyn-2-yl)-N''-(2-mercaptoethyl)guanidine, and the title product is thereby produced.

EXAMPLE 6

N-Cyano-N'-{2-[(4-methyl-5-imidazolyl)methylthio]ethyl}-N''-(3-butyn-2-yl)guanidine

A.
N-Cyano-N'-(3-butyn-2-yl)-N''-(2-mercaptoethyl)guanidine

The general procedures of Example 1, steps A and B, are repeated except that the propargylamine utilized in step A thereof is replaced by an equimolar amount of 1-methylpropargylamine, and the title product is thereby produced.

B.
N-Cyano-N'-{2-[(4-methyl-5-imidazolyl)methylthio]ethyl}-N''-(3-butyn-2-yl)guanidine The general procedure of Example 1C is repeated except that the N-cyano-N'-propargyl-N''-(2-mercaptoethyl)guanidine utilized therein is replaced by an equimolar amount of N-cyano-N'-(3-butyn-2-yl)-N''-(2-mercaptoethyl)guanidine, and the title product is thereby produced.

We claim:

1. A compound of the formula

wherein $R^1$ is a straight or branched chain alkynyl group containing from 3 to 9 carbon atoms, or an acid addition salt thereof.

2. A compound of claim 1 having the formula

wherein $R^4$ is hydrogen or methyl, or an acid addition salt thereof.

3. A compound of claim 1 having the formula

wherein $R^4$ is hydrogen or methyl and n is an integer of from 1 to 6, inclusive, or an acid addition salt thereof.

4. A compound of claim 1 having the formula

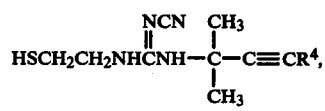

wherein $R^4$ is hydrogen or methyl, or an acid addition salt thereof.

5. N-Cyano-N'-propargyl-N''-(2-mercaptoethyl)-guanidine, or an acid addition salt thereof.

6. N-Cyano-N'-(2-butyn-1-yl)-N''-(2-mercaptoethyl)guanidine, or an acid addition salt thereof.

7. N-Cyano-N'-(3-butyn-1-yl)-N''-(2-mercaptoethyl)guanidine, or an acid addition salt thereof.

8. N-Cyano-N'-(3-butyn-2-yl)-N''-(2-mercaptoethyl)guanidine, or an acid addition salt thereof.

9. N-Cyano-N'-(4-pentyn-1-yl)-N''-(2-mercaptoethyl)guanidine, or an addition salt thereof.

10. N-Cyano-N'-(2-methyl-3-butyn-2-yl)-N''-(2-mercaptoethyl)guanidine, or an acid addition salt thereof.

* * * * *